United States Patent [19]

Sato et al.

[11] Patent Number: 5,461,173
[45] Date of Patent: Oct. 24, 1995

[54] FLUORINE-CONTAINING ORGANOSILICON COMPOUND AND ITS MANUFACTURE

[75] Inventors: Shinichi Sato; Takashi Matsuda; Takafumi Sakamoto; Masatoshi Arai, all of Matsuida, Japan

[73] Assignee: Shin-Etsu Chemical Co., Ltd., Tokyo, Japan

[21] Appl. No.: 364,448

[22] Filed: Dec. 27, 1994

[30] Foreign Application Priority Data

Dec. 27, 1993 [JP] Japan .................. 5-351847
Dec. 27, 1993 [JP] Japan .................. 5-351848

[51] Int. Cl.$^6$ ............... C07F 7/08; C07F 7/10; C07F 7/18
[52] U.S. Cl. ............... 556/439; 556/419; 556/422; 556/438
[58] Field of Search ............... 556/419, 422, 556/438, 439

[56] References Cited

U.S. PATENT DOCUMENTS

| | | |
|---|---|---|
| 3,423,234 | 1/1969 | Heine . |
| 3,442,664 | 4/1966 | Heine . |
| 3,646,085 | 2/1972 | Bartlett . |
| 3,666,538 | 10/1972 | Domba . |
| 3,716,517 | 2/1973 | Pittman et al. ............ 556/438 X |
| 3,772,346 | 3/1972 | Hess . |
| 3,810,874 | 9/1972 | Mitsch . |
| 3,950,588 | 11/1974 | McDougal . |
| 4,094,911 | 6/1978 | Mitsch et al. . |
| 4,689,181 | 8/1987 | Blatch ............ 556/438 X |
| 5,385,999 | 1/1995 | D'Anvers et al. ............ 556/439 X |

Primary Examiner—Paul F. Shaver
Attorney, Agent, or Firm—Cushman Darby & Cushman

[57] ABSTRACT

A fluorine-containing organosilicon compound represented by the following general formula (1):

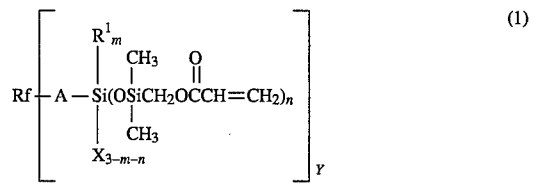

wherein Rf represents a perfluoroalkyl group, a perfluorooxyalkyl group, a perfluoroalkylene group, or a perfluorooxyalkylene group, A represents a bivalent organic group, $R^1$ represents an unsubstituted or substituted monovalent hydrocarbon group, X represents a hydrolyzable group, Y is 1 in the case where the above group Rf represents a perfluoroalkyl group or a perfluorooxyalkyl group or Y is 2 in the case where the above group Rf represents a perfluoroalkylene group or a perfluorooxyalkylene group, m is an integer of 0 to 2, and n is an integer of 1 to 3, with m+n being 3 or less. Since this compound has an acryloyloxy group(s), the compound when irradiated with ultraviolet light can be easily cured within a short period of time, for example, within about 1 to 2 min in the presence of a photopolymerization initiator.

20 Claims, 8 Drawing Sheets

FLUORINE-CONTAINING ORGANOSILICON COMPOUND AND ITS MANUFACTURE

BACKGROUND OF THE INVENTION

1. Field of the Invention

The present invention relates to a novel organosilicon compound that has a fluorine-containing group and an acryloyloxy group.

2. Description of the Prior Art

Conventionally, fluorine-containing organosilicon compounds having a silyl group with a hydrolyzable group bonded to the silicon atom are used as a lubricant and a surface coating agent for metals, glasses, various plastics, and the like. That is, these compounds when applied to a base surface form a cured coating on the base surface by the hydrolysis/condensation reaction with moisture in the air.

SUMMARY OF THE INVENTION

Since the above fluorine-containing organosilicon compounds have a silicon-bonded hydrolyzable group, they exhibit good adhesion to various bases, but after the completion of the hydrolysis/condensation reaction it requires not less than 2 or 3 hours at normal temperatures to cure and even if they are heated to about 100° C., it requires 10 to 20 min to cure, and therefore more quick curing, particularly at normal temperatures, is desired.

Incidentally, since the hydrolysis rate of the silicon-bonded hydrolyzable group possessed by such a compound increases as the number of the hydrolyzable groups increases, say, from one to two and from two to three, in order to acquire quick curability, it is recommended to increase the number of the hydrolyzable groups. However, when the compound having a silicon-bonded hydrolyzable group comes in contact with the air during its storage, part of the compound is hydrolyzed with moisture in the air to form a gel sometimes. Therefore there is the problem that as the number of the hydrolizable groups increases, a gel is liable to be formed and care must be taken to handle such a compound.

Therefore, an object of the present invention is to provide a fluorine-containing organosilicon compound that has good quick curability and is less liable to form a gel.

According to the present invention, there is provided a fluorine-containing organosilicon compound represented by the following general formula (1):

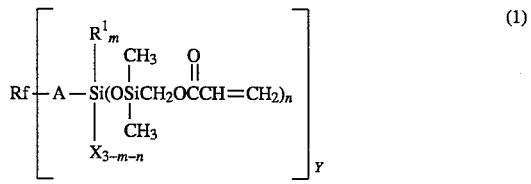

wherein Rf represents a perfluoroalkyl group, a perfluorooxyalkyl group, a perfluoroalkylene group, or a perfluorooxyalkylene group, A represents a bivalent organic group, $R^1$ represents an unsubstituted or substituted monovalent hydrocarbon group, X represents a hydrolyzable group, Y is 1 in the case where the above group Rf represents a perfluoroalkyl group or a perfluorooxyalkyl group or Y is 2 in the case where the above group Rf represents a perfluoroalkylene group or a perfluorooxyalkylene group, m is an integer of 0 to 2, and n is an integer of 1 to 3, with m+n being 3 or less.

According to the present invention, there is also provided a method of producing a fluorine-containing organosilicon compound represented by the above general formula (1), comprising reacting a hydrolyzable silane compound represented by the following general formula (2):

wherein Rf, A, m, $R^1$, X, and Y have the same meanings as defined above in the above general formula (1) with a silane compound represented by the following general formula (3):

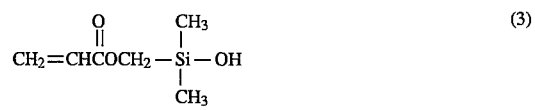

in the presence of a condensation catalyst.

Since the compound of the present invention has an acryloyl group(s), the compound when irradiated with ultraviolet light can be easily cured within a short period of time, for example, within about 1 to 2 min in the presence of a photopolymerization initiator. Where the compound has a hydrolyzable group X, the quick curability with irradiation with ultraviolet light as well as the adhesion to various bases can be made favorable.

DETAILED DESCRIPTION OF PREFERRED EMBODIMENTS

Fluorine-containing organosilicon compounds

Figure 1:
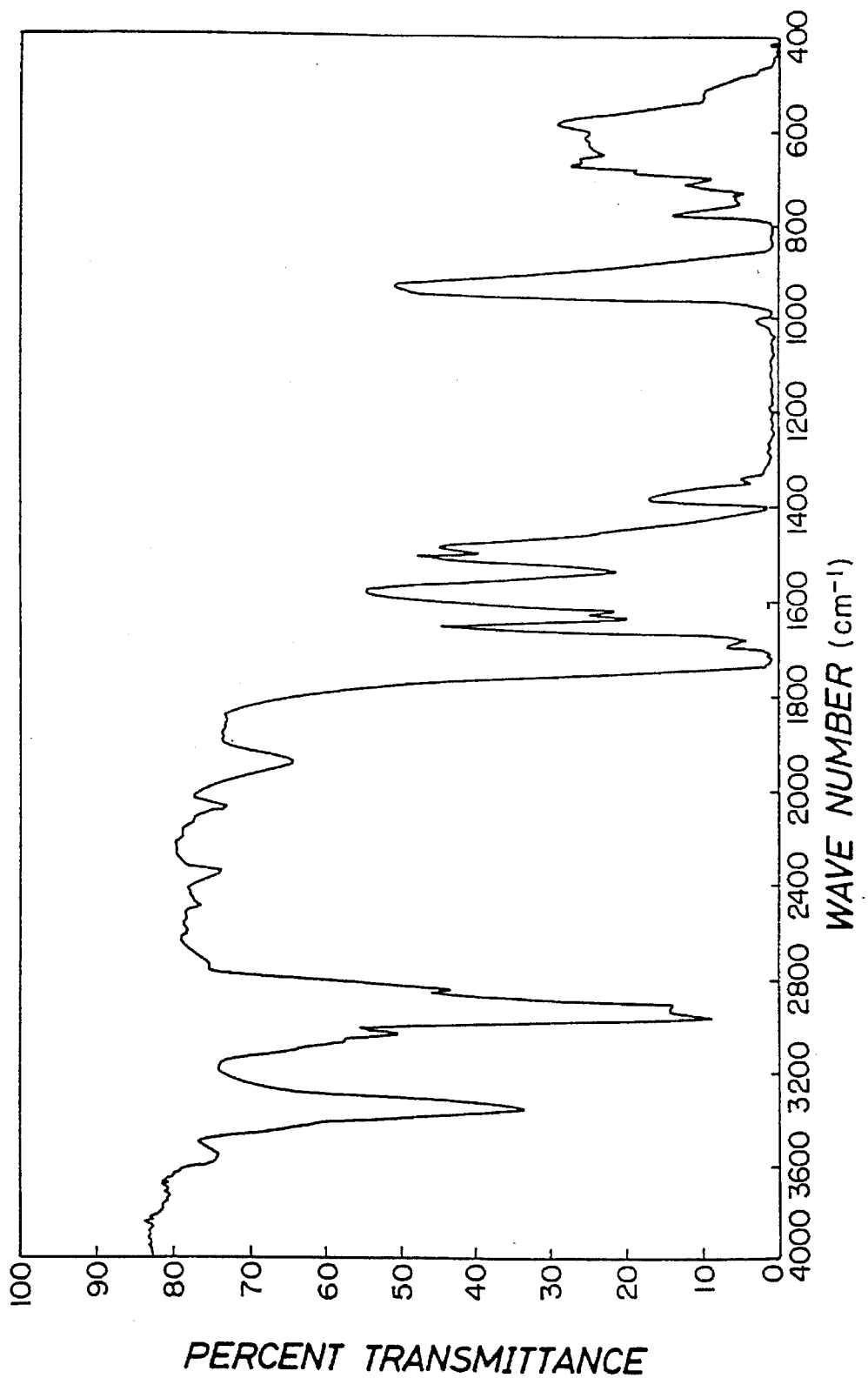
FIG. 1 is an IR chart of the compound of the present invention obtained in Example 1.

As represented by the above general formula (1), in the present fluorine-containing organosilicon compound, part or all of the hydrolyzable groups X is (are) replaced by a siloxy group(s) containing an acryloyl group, i.e., an acryloyloxymethyldimethylsiloxy group (s) . That is, since an acryloyl group(s) is (are) introduced, upon irradiation with ultraviolet light this compound can be easily cured instantaneously in the presence of a photopolymerization initiator. For example, the compound is cured in 1 to 2 min at normal temperatures upon irradiation with ultraviolet light. Accordingly, since the quick curability is acquired not by an increase in the number of hydrolyzable groups but by the replacement of the hydrolyzable group by the acryloyl-group-containing siloxy group, during the storage the compound is prevented effectively from forming a gel.

In the present compound, the number n of the acryloyl-group-containing siloxy groups can be set in the range of 1 to 6 without any restriction. For example, if the hydrolyzable group X is retained (in the case that 3–m–n that shows the number of the hydrolyzable groups, or the below-mentioned value of 3–p–q is positive), the compound can be cured with moisture in the air, that is, the compound has two advantages, the quick curability by irradiation with ultraviolet light and the adhesion to various bases by the hydrolyzable group.

Further, since the present fluorine-containing organosilicon compound has a monovalent or bivalent fluorine-containing group (Rf), the present fluorine-containing organosilicon compound has such properties as chemical resistance, water/oil repellency, low-surface tension, and non-staining properties and can be used, for example, as resin modifiers, paint additives, coating agents, releasing agents, and antisoiling agents for sealants. For example, in the case where all of the hydrolyzable groups (X) are replaced by acryloyl-group-containing siloxy groups (in the case wherein the below-mentioned 3–p–q=0 and/or 3–m–n=0), the compound can be used for resin modifiers, releasing agents, and the like.

The present fluorine-containing organosilicon compound represented by the above general formula (1) includes a fluorine-containing organosilicon compound represented by the following general formula (4):

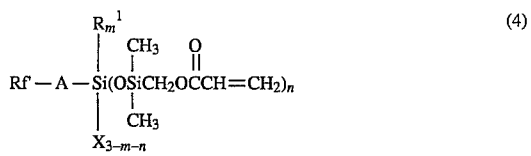

(4)

wherein Rf' represents a perfluoroalkyl group or a perfluorooxyalkyl group and A, $R^1$, X, m, and n have the same meanings as defined above and a fluorine-containing organosilicon compound represented by the following general formula (5):

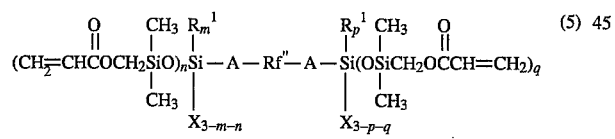

(5)

wherein Rf" represents a perfluoroalkylene group or a perfluorooxyalkylene group, p is an integer of 0 to 2, q is an integer of 1 to 3, with p+q being 3 or less, A each independently represent a bivalent organic group, $R^1$ each independently represent an unsubstituted or substituted monovalent hydrocarbon group, X each independently represent a hydrolyzable group, and m and n have the same meanings as defined above.

In the case wherein Y is 1 in the above general formula (1) or in the case of the above general formula (4), Rf and Rf' each represent a perfluoroalkyl group or a perfluorooxyalkyl group, which preferably has 1 to 30 carbon atoms, and particularly preferably 1 to 15 carbon atoms. The perfluoroalkyl group is represented by the formula: $C_aF_{2a}+1$ wherein a is an integer of 1 to 30, and examples include a trifluoromethyl group, a pentafluoroethyl group, a heptafluoropropyl group, a nonafluoro-n-butyl group, a tridecafluoro-n-hexyl group, a heptadecafluoro-n-octyl group, an n-$C_{10}F_{21}$-group, and an n-$C_{12}F_{25}$- group, with preference given to a perfluoroalkyl group having 1 to 12 carbon atoms.

The perfluorooxyalkyl group is represented by the general formula: F—$(Rf^1O)_b$—$Rf^2$—wherein $Rf^1$ and $Rf^2$ each independently represent a straight-chain or branched perfluoroalkylene group having 1 to 3 carbon atoms and b is an integer of 1 to 10, and preferably 1 to 6, and specific examples include perfluorooxyalkyl groups represented by the following formulae:

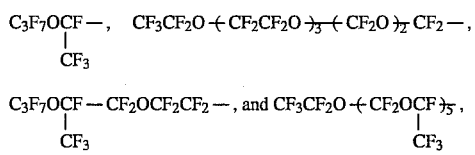

preference given to a perfluorooxyalkyl group having 2 to 20 carbon atoms.

In the case wherein Y is 2 in the above general formula (1) or in the case of the above general formula (5), Rf and Rf" each represent a perfluoroalkylene group or a perfluorooxyalkylene group, which preferably has 1 to 100 carbon atoms, and particularly preferably 2 to 50 carbon atoms.

This perfluoroalkylene group is a straight-chain or branched perfluoroalkylene group represented by —$C_cF_{2c}$— wherein c is an integer of 1 to 20, and typical examples include —$C_2F_4$—, —$C_3F_6$—, —$C_4F_8$—, —$C_5F_{10}$—, —$C_6F_{12}$—, —$C_8F_{16}$—, and —$C_{10}F_{20}$—, with preference given to a perfluoroalkylene group having 2 to 12 carbon atoms.

Further, the perfluorooxyalkylene group is a group represented by the following general formula:

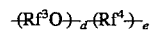

wherein $Rf^3$ and $Rf^4$ each independently represent a straight-chain or branched perfluoroalkylene group having 1 to 3 carbon atoms, d is an integer of 1 to 40, e is an integer of 0 to 3, and the arrangement of —$Rf^3O$— and —$Rf^4$— may be random, and specific examples include

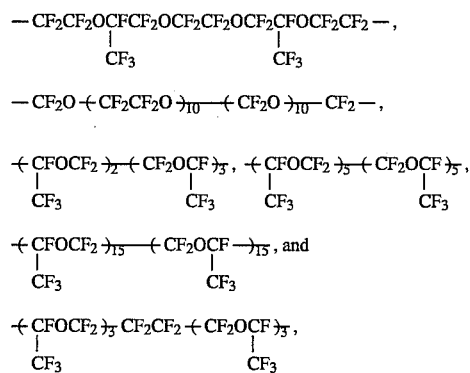

with preference given to a perfluorooxyalkylene group having 10 to 100 carbon atoms. Of course, in the above, the number of perfluorooxyalkylene blocks can be suitably changed. A represents a bivalent organic group and examples include a bivalent hydrocarbon group, for example, an alkylene group having 1 to 8 carbon atoms, such as a methylene group, an ethylene group, and a propylene group, an arylene group having 6 to 10 carbon atoms, such as a phenylene group, a tolylene group, a xylylene group, a naphthylene group, and a biphenylene group, and a group consisting of a combination of these alkylene groups with these arylene groups represented, for example, by the following formulas:

with preference given to a bivalent hydrocarbon group having 2 to 10 carbon atoms. The bivalent organic group A may contain heteroatoms and may be a group containing, for example, an ester linkage or a thioester linkage, such as —$CO_2$— and —$SO_3$—, an ether linkage or a thioether linkage, such as —O— and —S—, a ketone linkage, such as —CO—, or an amide linkage, such as —CONR— and —$SO_2$NR— wherein R represents a hydrogen atom or a monovalent hydrocarbon group having 1 to 6 carbon atoms.

Specific examples of such a group having heteroatoms include

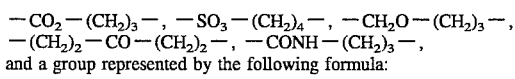

with preference given to

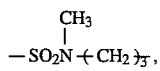

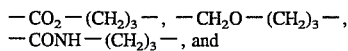

and

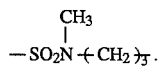

Preferably the unsubstituted or substituted monovalent hydrocarbon group $R^1$ has 1 to 8 carbon atoms and examples include an alkyl group, such as a methyl group, an ethyl group, and a propyl group; a cycloalkyl group, such as a cyclohexyl group; an alkenyl group, such as a vinyl group, an allyl group, and an isopropenoxy group; an aryl group, such as a phenyl group and a tolyl group; and corresponding monovalent substituted hydrocarbon groups in which part or all of the hydrogen atoms of the above monovalent hydrocarbon groups have been replaced with a halogen atom(s), such as a 3,3,3-trifluoropropyl group, a 3,3,4,4,5,5,6,6,6-nonafluorohexyl group, a chloromethyl group, and a 3-chloropropyl group, with preference given to an unsubstituted or substituted monovalent hydrocarbon group having 1 to 6 carbon atoms.

As the hydrolyzable group X, there are various hydrolyzable groups, and typical examples include hydrolyzable groups represented by the following formulas:

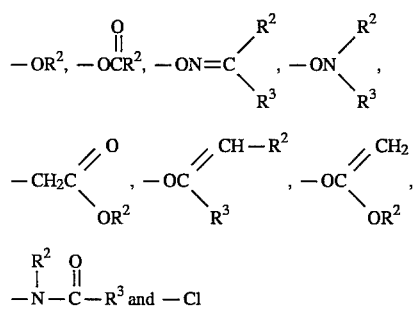

wherein $R^2$ and $R^3$ each represent a hydrogen atom or an unsubstituted or substituted monovalent hydrocarbon group having 1 to 6 carbon atoms, such as an alkyl group, e.g., a methyl group, an ethyl group, a propyl group, an isopropyl group, a butyl group, an isobutyl group, a tert-butyl group, a pentyl group, a hexyl group, and a cyclohexyl group, an alkenyl group, e.g., a vinyl group, an allyl group, a propenyl group, an isopropenyl group, a butenyl group, an isobutenyl group, a hexenyl group, and a cyclohexenyl group, an aryl group, e.g., a phenyl group, and a halogen-substituted alkyl group, e.g., a chloromethyl group, a 3-chloropropyl group, and a 3,3,3-trifluoropropyl group. Particularly preferably the hydrolyzable group X include a chlorine atom, a methoxy group, an ethoxy group, an acetoxy group, a propenoxy group, an isopropenoxy group, a diethylamino group, and

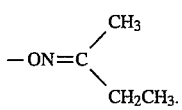

When the above silicon-containing organosilicon compound is combined with a photopolymerization initiator, which is known per se, such as acetophenone, propiophenone, benzophenone, xanthol, fluorene, benzaldehyde, anthraquinone, triphenylamine, 4-methylacetophenone, 3-pentylacetophenone, 4-methoxyacetophenone, 3-bromoacetophenone, 4-allylacetophenone, p-acetylbenzene, 3-methoxybenzophenone, 4-methylbenzophenone, 4-chlorobenzophenone, 4,4-dimethoxybenzophenone, 4-chloro-4-benzylbenzophenone, 3-chloroxanthone, 3,9-dichloroxanthone, 3-chloro-8-nonylxanthone, benzoin, benzoin methyl ether, benzoin butyl ether, bis (4-dimethylaminophenyl) ketone, benzyl methoxyketal, 2-chlorothioxanthone, diethylacetophenone, 1-hydroxycyclohexyl phenyl ketone, 2-methyl-[4-(methylthio)phenyl]-2-morpholino-1-propane, 2,2-dimethoxy-2-phenylacetophenone, and diethoxyacetophenone, and is irradiated with ultraviolet light, the silicon-containing organosilicon compound is immediately cured. Generally the amount of these photopolymerization initiators to be used may be about 0.01 to 10 parts by weight per 100 parts by weight of the above fluorine-containing organosilicon compound. In this case, optionally a sensitizer may be additionally used.

As described above, in the case where the hydrolyzable group X exists, the curing can be made with moisture in the air.

Preparation of the fluorine-containing organosilicon compound

The fluorine-containing organosilicon compound of the present invention is produced by reacting a hydrolyzable silane compound represented by the above general formula (2) with a silane compound represented by the above general formula (3), i.e., an acryloyloxymethyldimethylsilanol. This reaction proceeds, for example, according to the following reaction formula:

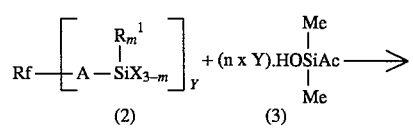

-continued

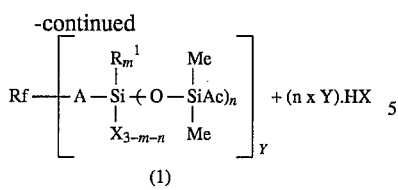

wherein Rf, A, X, R¹, m, n and Y have the same meanings as defined above, Me represents a methyl group, and Ac represents an acryloyloxymethyl group.

That is, the intended compound of the formula (1) and the by-product represented by the formula HX are obtained. It is enough that the temperature of this condensation reaction is from about room temperature to about 80° C. Since the by-product represented by HX sometimes reacts with the silanol, the raw material silane compound of the formula (3), the by-product produced by the reaction is preferably removed immediately outside the reaction system. Since this by-product is relatively low in boiling point, it is desirable that the reaction is effected under normal pressures or reduced pressure, and for example by carrying out the reaction under a reduced pressure of 20 mmHg to or 200 mmHg, the by-product can be easily removed outside the system.

As can be understood from the above reaction formula, by adjusting the amount of the silane compound of the general formula (3) to the hydrolyzable group X in the silane compound of the general formula (2), the degree of substitution by the acryloyl-group-containing siloxy group, i.e., an acryloyloxymethyldimethylsiloxy group. For example, by using the silane compound of the general formula (3) in excess stoichiometrically to the hydrolyzable group X, the remaining hydrolyzable group X can be brought to 0.

The silane compound of the above general formula (2) includes a silane compound represented by the following formula:

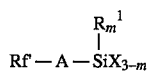

wherein Rf', A, X R¹ and m have the same meanings as defined above and a silane compound represented by the following formula:

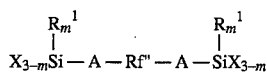

wherein Rf", A, X R¹ and m have the same meanings as defined above.

If required, by using a condensation catalyst, the above reaction can be caused to proceed more quickly. Such a condensation catalyst includes, for example, a metal salt of an organic carboxylic acid, such as lead 2-ethyl octoate, dibutyl tin diacetate, dibutyl tin dilaurate, butyl tin tri-2-ethylhexoate, iron 2-ethylhexoate, cobalt 2-ethylhexoate, manganese 2-ethylhexoate, zinc 2-ethylhexoate, stannous caprylate, tin naphthenate, tin oleate, tin butyrate, titanium naphthenate, zinc naththenate, cobalt naphthenate, and zinc stearate; an organic titanic acid ester, such as tetrabutyl titanate, tetra-2-ethylhexyl titanate, triethanolamine titanate, and tetra (isopropenyloxy) titanate; an organotitanium compound, such as an organosiloxy titanium and β-carbonyl titanium; a lower aliphatic acid salt of an alkali metal, such as potassium acetate, sodium acetate, and lithium oxalate; a dialkylhydroxyamine, such as dimethylhydroxyamine and diethylhydroxyamine; tetramethylquanidine, and a guanidine compound, such as, a guanidyl-group-containing silane or siloxane, for example, represented by the following formula (6) or (7):

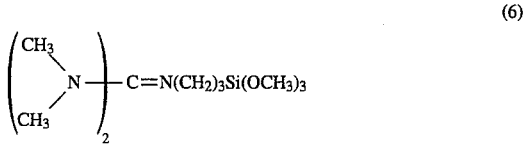

and

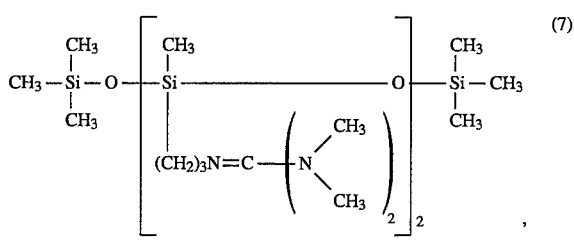

which may be used singly or as a combination of two or more. As the condensation catalyst, an organic carboxylic acid tin salt, an organic titanic acid ester, or a guanidyl compound is preferable.

The amount of these condensation catalysts to be added is about 0.001 to about 5.0 parts by weight per 100 parts by weight of the hydrolyzable silane compound of the general formula (2).

EXAMPLES

In the following Examples, Me denotes a methyl group and Et denotes an ethyl group.

Example 1

13.1 g of a fluorine-containing organosilicon compound represented by the following formula (2-1):

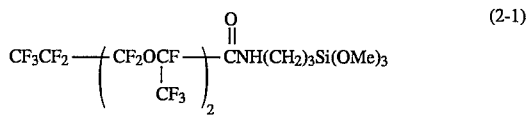

and 0.005 g of a guanidine derivative (condensation catalyst) represented by the above formula (6) were charged into a 100-ml three-necked flask equipped with a stirrer, a thermometer, a dropping funnel and connected to a vacuum line through a Liebig condenser. The internal atmosphere of the flask was replaced with dry $N_2$ quickly and the resulting mixture was heated slowly with stirring to bring the internal temperature to 50° C.

Then, 19.2 g of a solution containing 50% of an organosilicon compound represented by the following formula (3-1):

in toluene was placed in the dropping funnel and the dropping funnel was set to the above 100-ml three-necked flask.

Thereafter, while the pressure of the inside of the three-necked flask was being reduced to 120 mmHg, the organosilicon compound of the formula (3-1) was added dropwise over about 10 min. After the completion of the addition, the resulting mixture was ripened for about 20 min, and then the pressure of the inside of the system was reduced to 3 mmHg to distill off the solvent and low-boiling components completely, thereby obtaining 31.5 g of a pale yellow transparent liquid. This product was analyzed by $^1$H-NMR, $^{19}$F-NMR, and IR and the following results were obtained:

$^1$H—NMR: (TMS standard)

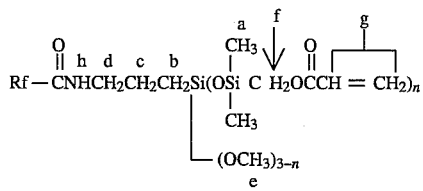

a: 0.15 ppm (s, 17.10H)
b: 0.51 ppm (m, 2H)
c: 1.60 ppm (m, 2H)
d: 3.33 ppm (m, 2H)
e: 3.45 ppm (s, 0.45H)
f: 3.72 ppm (s, 5.70H)
g: 5.5 to 6.5 ppm (m, 8.55H)
h: 7.48 ppm (bs, 1H)

$^{19}$F—NMR: (CF$_3$COOH standard)

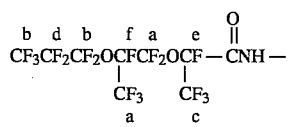

a: −3.65 ppm
b: −5.11 ppm
c: −6.04 ppm
d: −52.63 ppm
e: −55.76 ppm
f: −67.97 ppm IR: The chart is shown in FIG. 1.
The characteristic absorptions were as follows:

νN—H: 3,350 cm$^{-1}$

νc=O (acryloyl): 1,725 cm$^{-1}$

νc=o (amido): 1,710 cm$^{-1}$

νc=c: 1,635 cm$^{-1}$

From the above results, it was confirmed that the obtained compound is represented by the following formula:

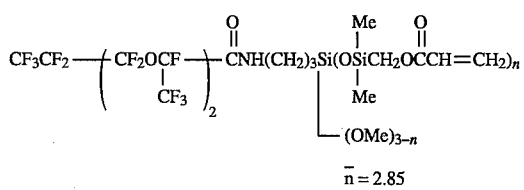

$\bar{n} = 2.85$

Example 2

The procedure was the same as in Example 1, except that in place of the fluorine-containing organosilicon compound represented by the above formula (2-1), 18.1 g of a fluorine-containing organosilicon compound represented by the following formula (2-2):

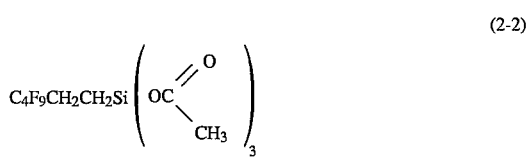

(2-2)

and in place of the guanidine derivative (condensation catalyst) represented by the above formula (6), 0.05 g of a dibutyl tin diacetate (condensation catalyst) were charged into a 100-ml three-necked flask, and 29.5 g of a 50 % solution of the organosilicon compound of the formula (3-1) used in Example 1 in toluene was placed in a dropping funnel, thereby obtaining 28.3 g of a colorless transparent liquid. This was analyzed by 1H-NMR, 19F-NMR, and IR and the following results were obtained:

$^1$H—NMR: (TMS standard)

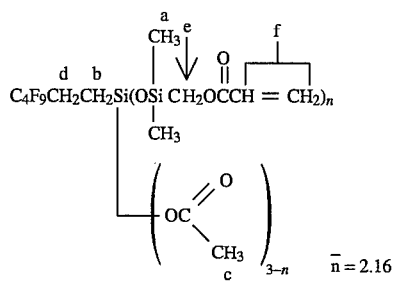

$\bar{n} = 2.16$ a: 0.17 ppm (s, 12.96H)
b: 0.86 ppm (m, 2H)
c: 1.97 ppm (s, 2.52H)
d: 2.22 ppm (m, 2H)
e: 3.74 ppm (s, 4.32H)
f: 5.5 to 6.5 ppm (m, 6.48H)

$^{19}$F—NMR: CF$_3$COOH standard

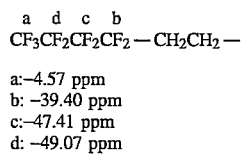

a: −4.57 ppm
b: −39.40 ppm
c: −47.41 ppm
d: −49.07 ppm

Figure 2:
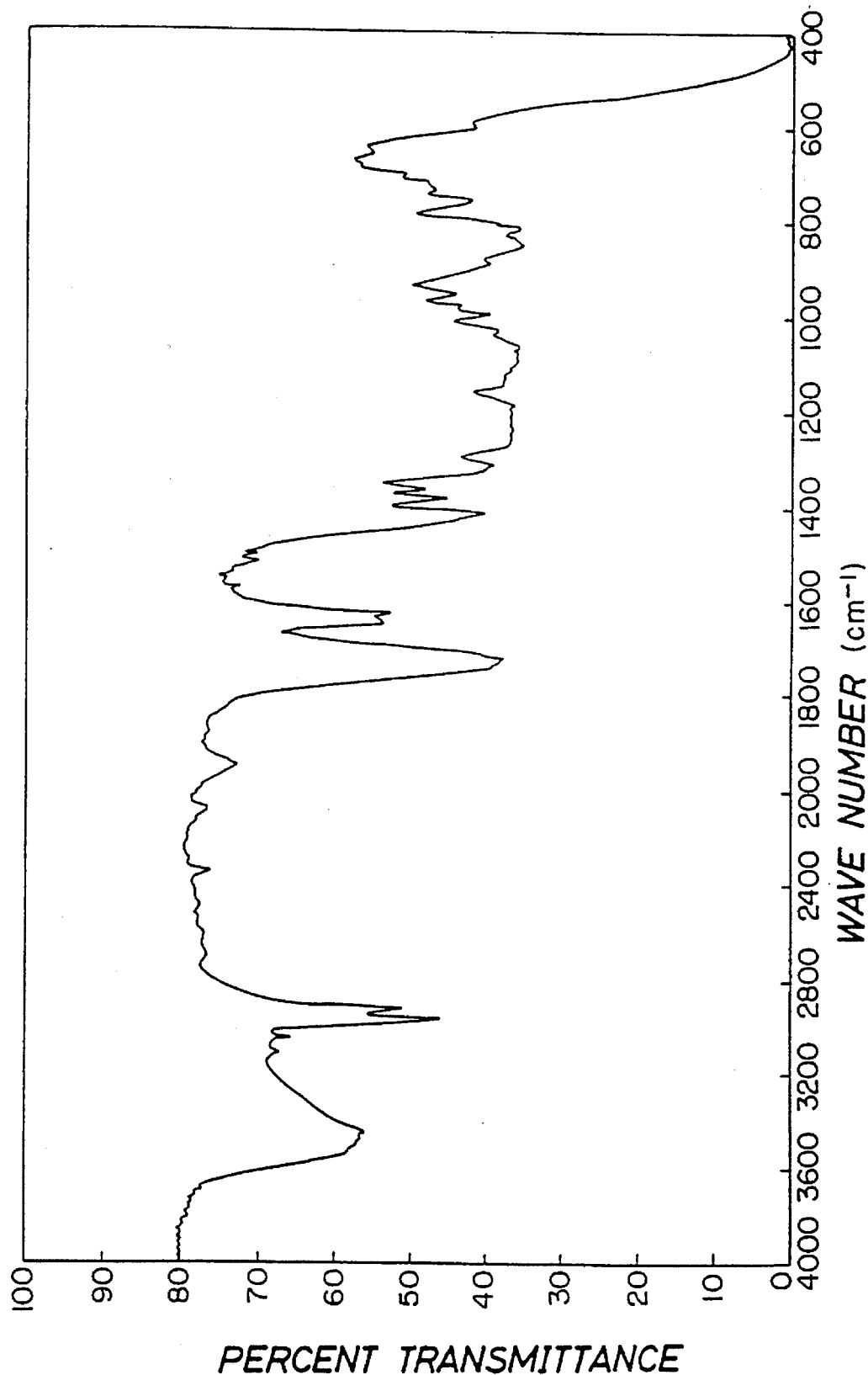
FIG. 2 ms an IR chart of the compound of the present invention obtained in Example 2.

IR: the chart is shown in FIG. 2.
The characteristic absorptions were as follows:

νc=o (acryloyl): 1,720 cm$^{-1}$

νc=o (Si-OCO-): 1,700 cm$^{-1}$

νc=o: 1,635 cm$^{-1}$

νC—F: 1,100 to 1,300 cm$^{-1}$

From the above results, it was confirmed that the obtained compound is represented by the following formula:

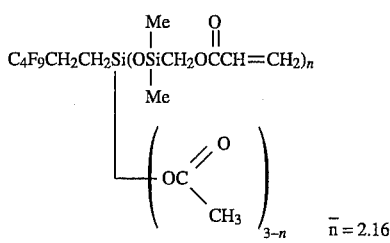

$\bar{n} = 2.16$

Example 3

The procedure was the same as in Example 1, except that in place of the fluorine-containing organosilicon compound represented by the above formula (2-1), 15.3 g of a fluorine-containing organosilicon compound represented by the following formula (2-3):

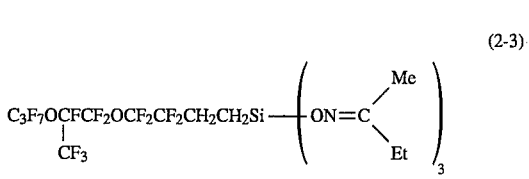
(2-3)

and in place of the guanidine derivative (condensation catalyst) represented by the above formula (6), 0.04 g of a dibutyl tin dilaurate (condensation catalyst) were charged into a 100-ml three-necked flask, and 13.0 g of a 50% solution of the organosilicon compound of the formula (3-1) used in Example 1 in toluene was placed in a dropping funnel, thereby obtaining 20.8 g of a pale yellow transparent liquid. This was analyzed by $^1$H-NMR, $^{19}$F-NMR, and IR and the following results were obtained:

$^1$H—NMR: (TMS standard)

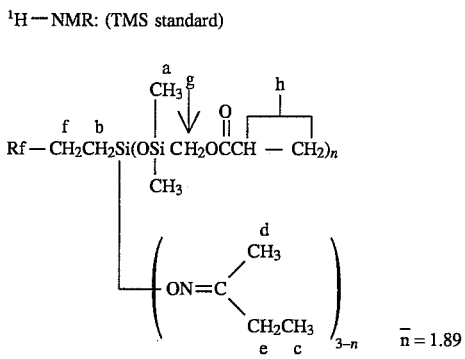

$\bar{n} = 1.89$ a: 0.17 ppm (s, 11.34H)
b: 0.90 ppm (m, 2H)
c: 1.02 ppm (t, 3.33H)
d: 1.82 ppm (s, 3.33H)
e: 2.25 ppm (q, 0.74H)
f: 2.31 ppm (m, 2H)
g: 3.73 ppm (s, 3.78H)
h: 5.5 to 6.5 ppm (m, 5.67H)

$^{19}$F—NMR: CF$_3$COOH standard

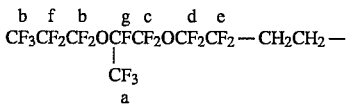

a: −3.35 ppm
b: −4.82 ppm
c: −6.63 ppm

-continued d: −10.78 ppm
e: −43.11 ppm
f: −52.54 ppm
g: −68.07 ppm

Figure 3:
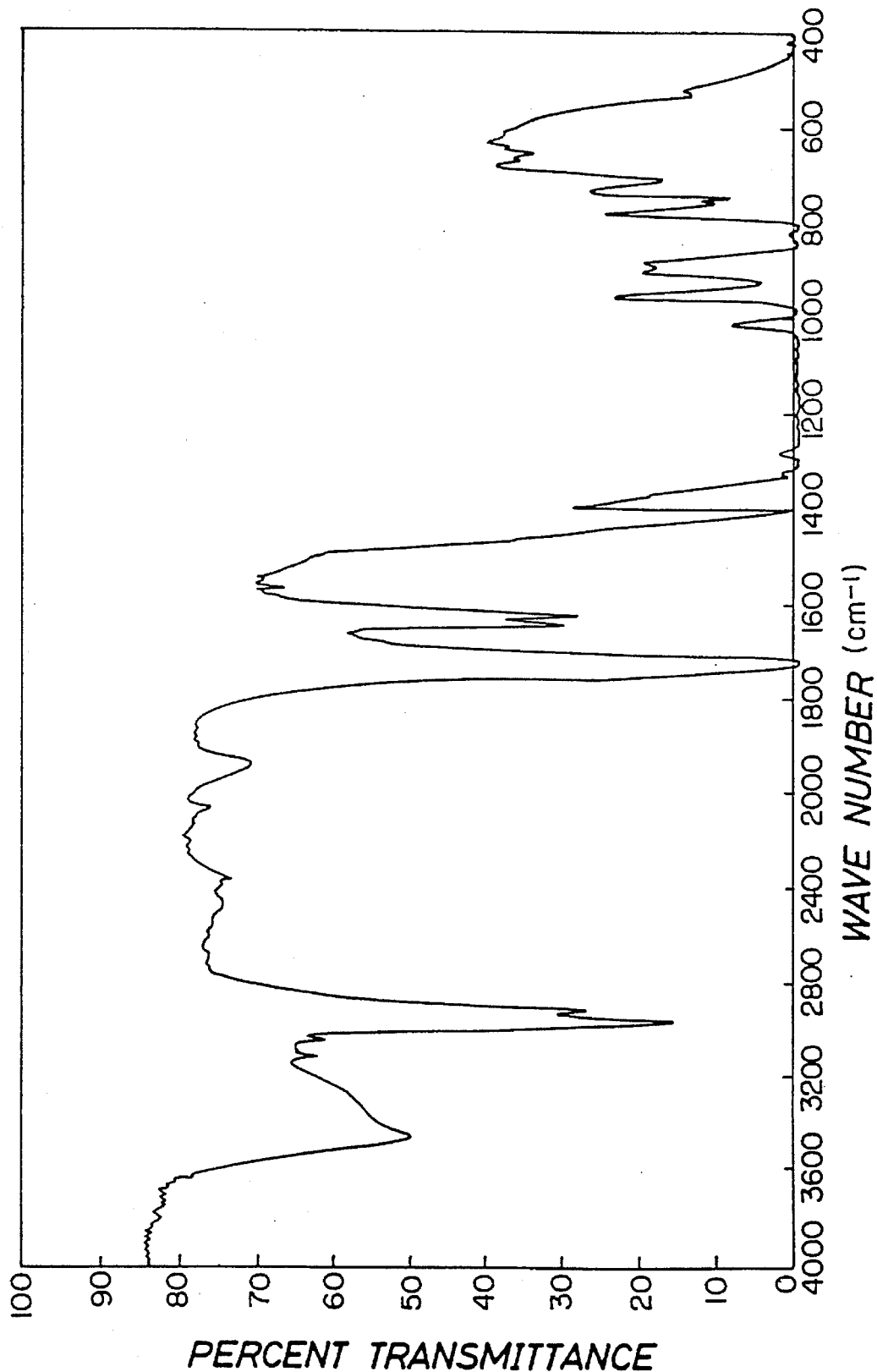
FIG. 3 is an IR chart of the compound of the present invention obtained in Example 3.

IR: the chart is shown in FIG. 3.
The characteristic absorptions were as follows:
νc=o: 1,725 cm$^{-1}$
νc=c: 1,635 cm$^{-1}$
νC—F: 1,100 to 1,300 cm$^{-1}$ From the above results, it was confirmed that the obtained compound is represented by the following formula:

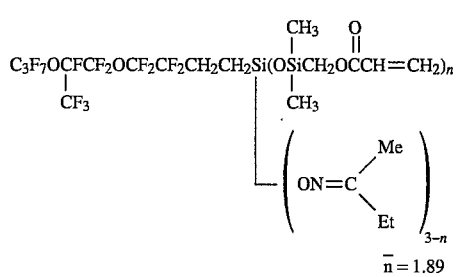

$\bar{n} = 1.89$

Example 4

The procedure was the same as in Example 1, except that in place of the fluorine-containing organosilicon compound represented by the above formula (2-1), 21.4 g of a fluorine-containing organosilicon compound represented by the following formula (2-4):

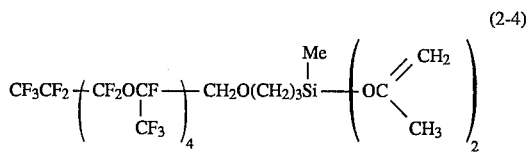
(2-4)

and in place of the guanidine derivative (condensation catalyst) represented by the above formula (6), 0.01 g of a guanidine derivative (condensation catalyst) represented by the above formula (7) were charged into a 100-ml three-necked flask, and 13.0 g of a 50 % solution of the organosilicon compound of the formula (3-1) used in Example 1 in toluene was placed in a dropping funnel, thereby obtaining 26.9 g of a pale yellow transparent liquid. This was analyzed by 1H-NMR, 19F-NMR, and IR and the following results were obtained:

$^1$H—NMR: (TMS standard)

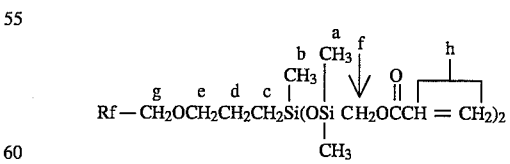

a: 0.17 ppm (s, 12H)
b: 0.22 ppm (m, 3H)
c: 0.59 ppm (m, 2H)
d: 1.66 ppm (m, 2H)
e: 3.57 ppm (t, 2H)
f: 3.74 ppm (s, 4H)
g: 4.04 ppm (d, 2H)

-continued h: 5.5 to 6.5 ppm (m, 6H)

$^{19}F$—NMR: $CF_3COOH$ standard

Figure 4:
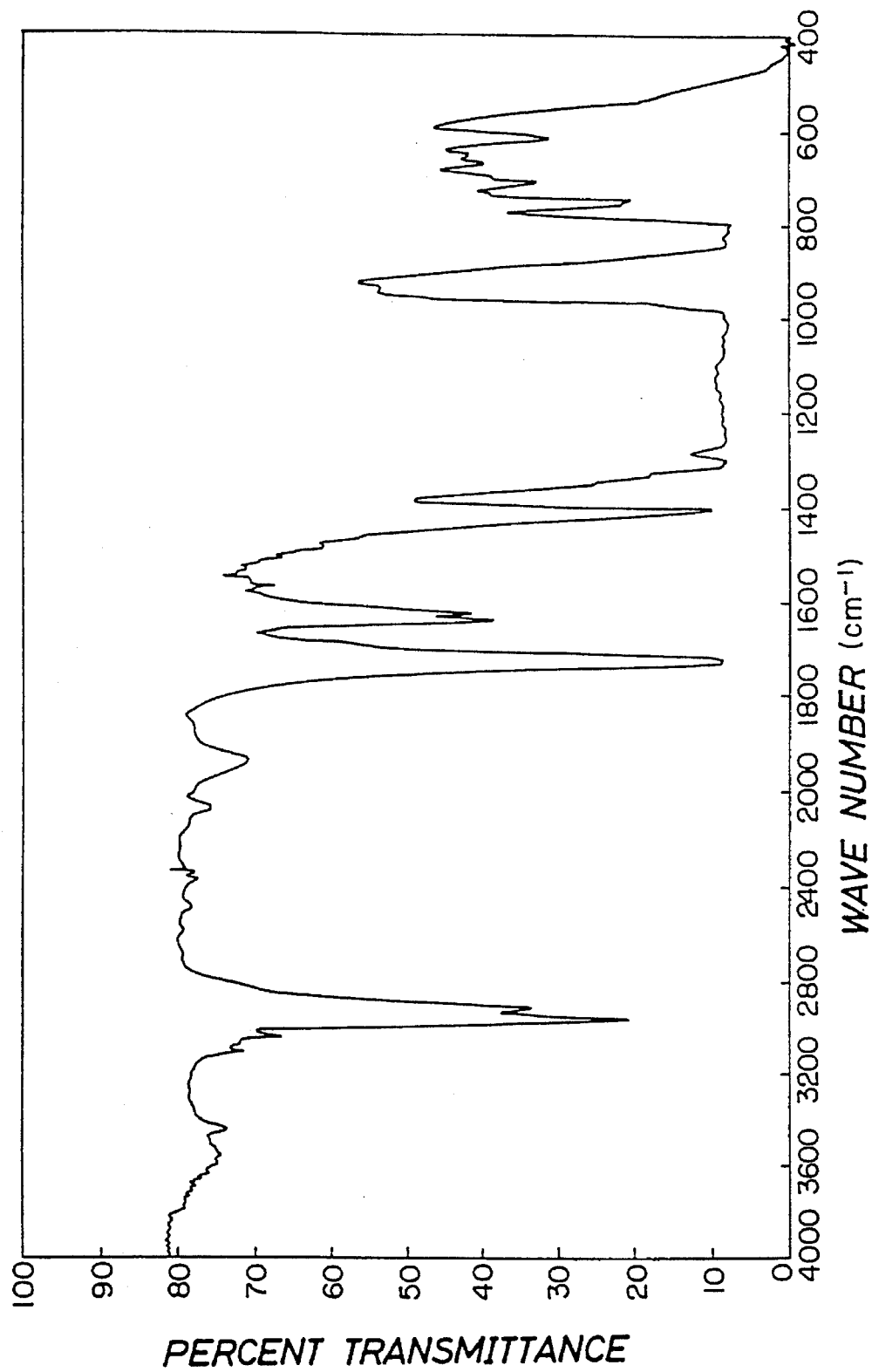
FIG. 4 is an IR chart of the compound of the present invention obtained in Example 4.

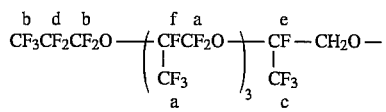

a: −3.40 ppm
b: −4.72 ppm
c: −5.84 ppm
d: −52.44 ppm
e: −55.66 ppm
f: −67.58 ppm IR: the chart is shown in FIG. 4.

The characteristic absorptions were as follows:

$vc=o$: 1,725 cm$^{-1}$ $vc=c$: 1,635 cm$^{-1}$ $vC-F$: 1,100 to 1,300 cm$^{-1}$

From the above results, it was confirmed that the obtained compound is represented by the following formula:

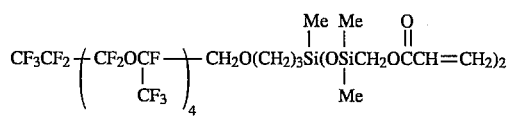

Example 5

The procedure was the same as in Example 1, except that in place of the fluorine-containing organosilicon compound represented by the above formula (2-1), 13.1 g of a fluorine-containing organosilicon compound represented by the following formula (2-5):

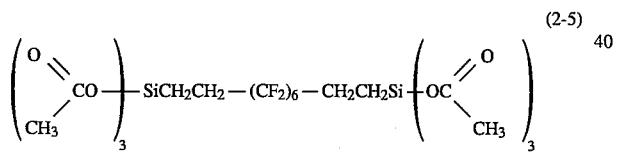

and in place of the guanidine derivative (condensation catalyst) represented by the above formula (6), 0.05 g of a dibutyl tin diacetate (condensation catalyst) were charged into a 100-ml three-necked flask, and 19.9 g of a 50 % solution of the organosilicon compound of the formula (3-1) used in Example 1 in toluene was placed in a dropping funnel, thereby obtaining 23.3 g of a colorless transparent liquid. This was analyzed by $^1$H-NMR, $^{19}$F-NMR, and IR and the following results were obtained:

$^1$H—NMR: TMS standard

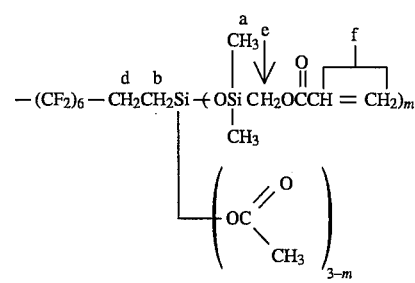

-continued a: 0.17 ppm (s, 17.58H)
b: 0.90 ppm (m, 4H)
c: 1.95 ppm (s, 9.21H)
d: 2.25 ppm (m, 4H)
e: 3.73 ppm (s, 5.86H)
f: 5.5 to 6.5 ppm (m, 8.79H)

$^{19}F$—NMR: $CF_3COOH$ standard $$-\overset{c}{CF_2}\overset{b}{CF_2}\overset{a}{CF_2}-CH_2CH_2-$$

a: −38.42 ppm
b: −44.28 ppm
c: −45.80 ppm

Figure 5:
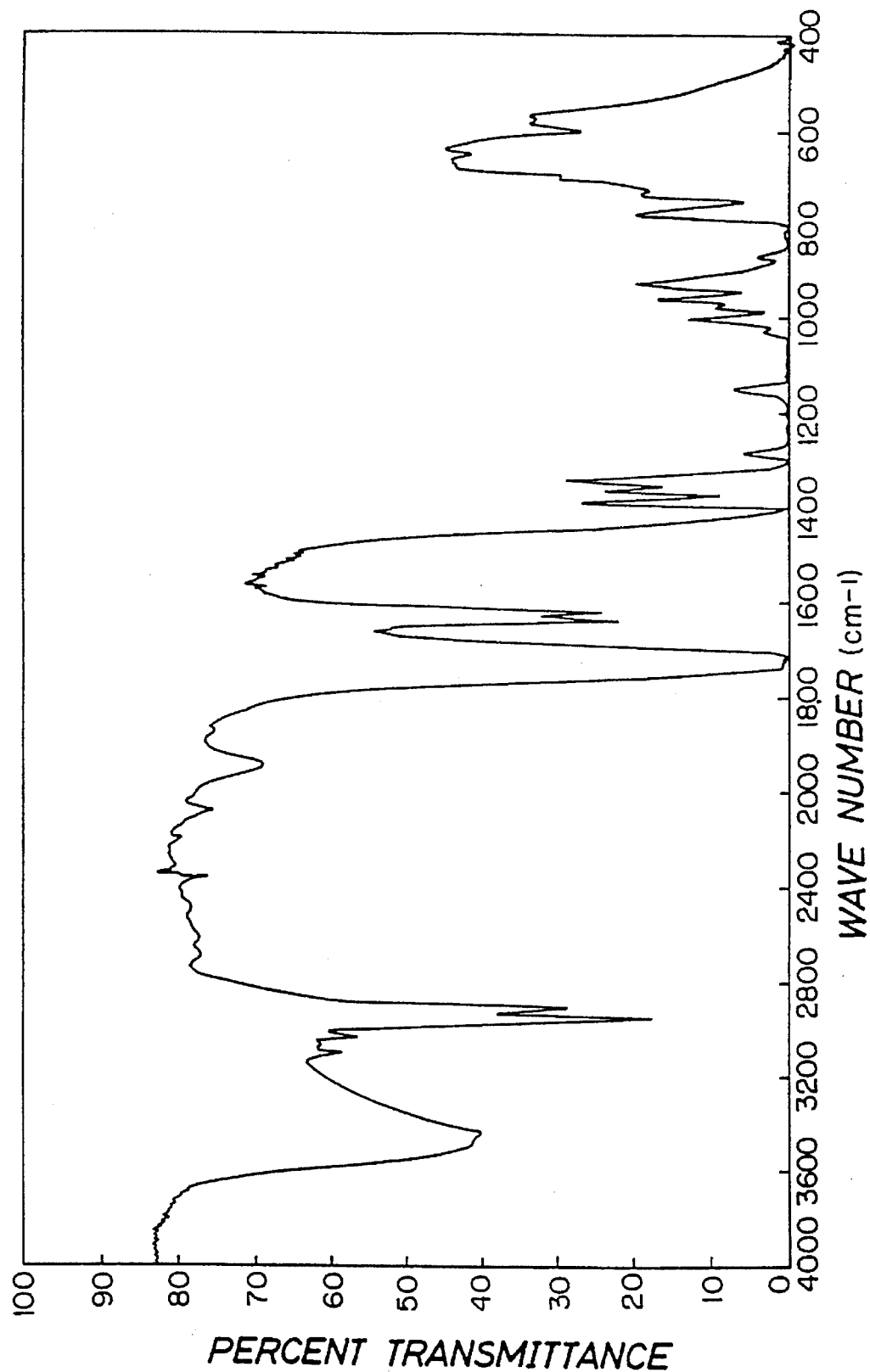
FIG. 5 ms an IR chart of the compound of the present invention obtained in Example 5.

IR: the chart is shown in FIG. 5.

The characteristic absorptions were as follows:

$vc=o$ (acryloyl): 1,725 cm$^{-1}$ $vc=o$ (SiOCO-): 1,700 cm$^{-1}$ $vc=c$: 1,635 cm$^{-1}$ $vC-F$: 1,100 to 1,300 cm$^{-1}$ From the above results, it was confirmed that the obtained compound is represented by the following formula:

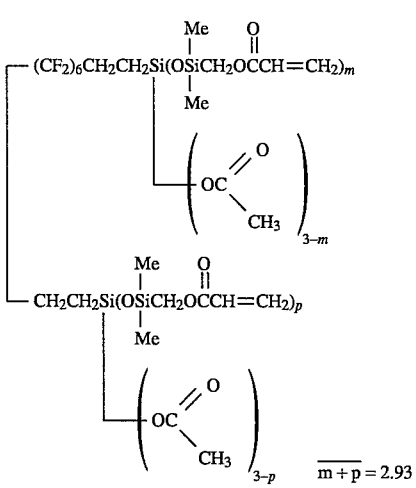

$\overline{m+p} = 2.93$

Example 6

The procedure was the same as in Example 1, except that in place of the fluorine-containing organosilicon compound represented by the above formula (2-1), 31.4 g of a fluorine-containing organosilicon compound represented by the following formula (2-6):

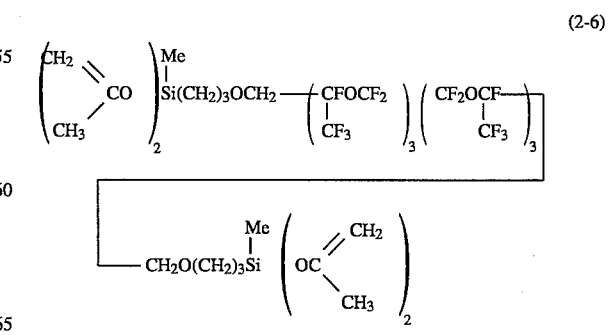

and 0.01 g of the guanidine derivative (condensation catalyst) represented by the above formula (6) were charged into a three-necked flask, and 27.2 g of a 50% solution of the organosilicon compound of the formula (3-1) used in Example 1 in toluene was placed in a dropping funnel, thereby obtaining 43.5 g of a colorless transparent liquid. This was analyzed by $^1$H-NMR, $^{19}$F-NMR, and IR and the following results were obtained:

$^1$H—NMR: TMS standard

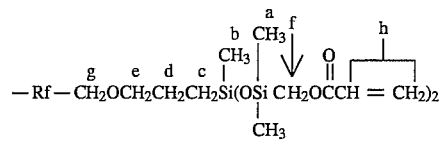

a: 0.17 ppm (s, 24H)
b: 0.21 ppm (s, 6H)
c: 0.59 ppm (m, 4H)
d: 1.64 ppm (m, 4H)
e: 3.55 ppm (t, 4H)
f: 3.70 ppm (s, 8H)
g: 4.00 ppm (d, 4H)
h: 5.5 to 6.5 ppm (m, 12H)

$^{19}$F—NMR: CF$_3$COOH standard

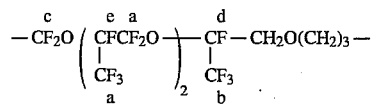

a: −3.60 ppm
b: −6.19 ppm
c: −9.36 ppm
d: −52.05 ppm
e: −67.87 ppm

Figure 6:
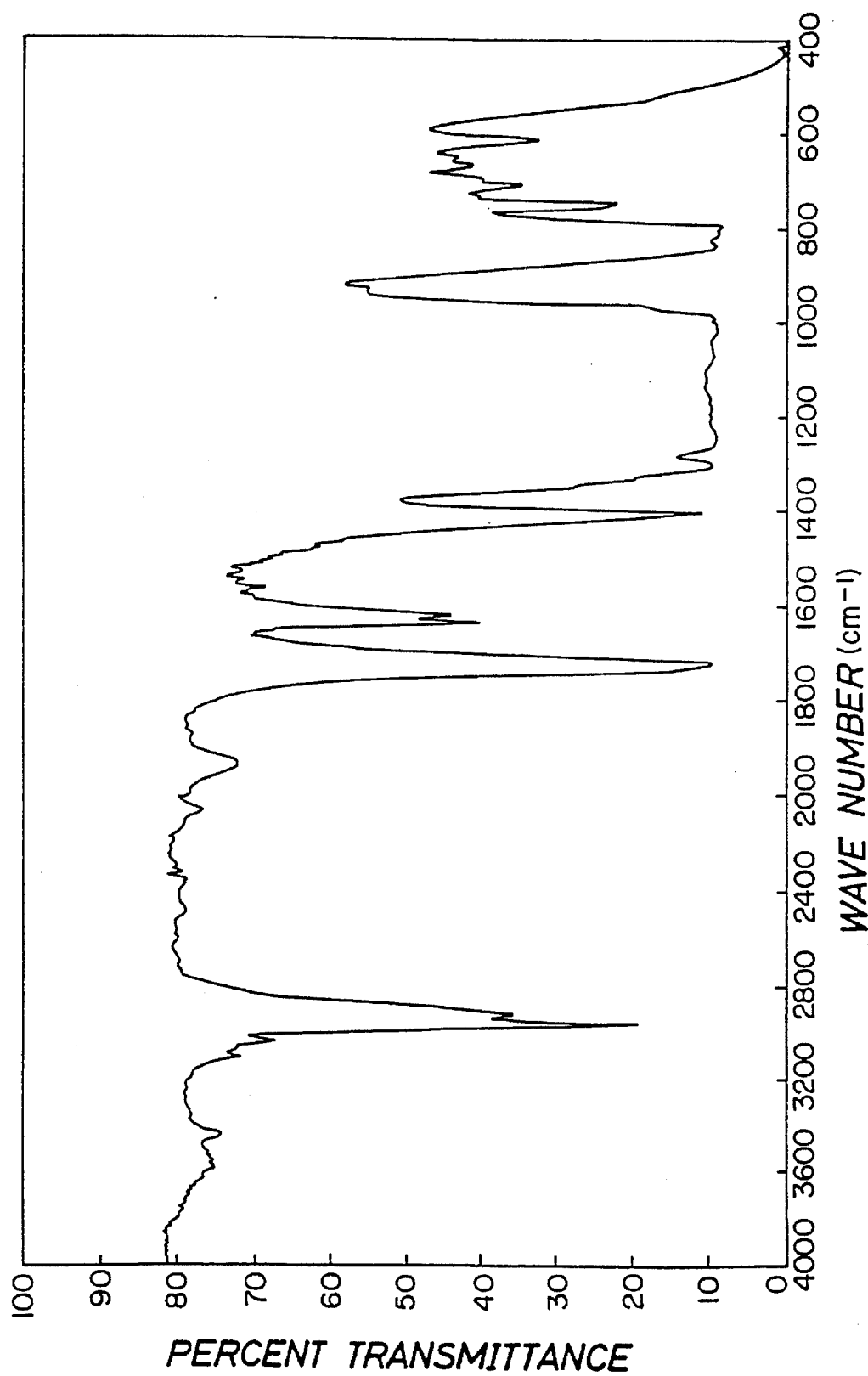
FIG. 6 is an IR chart of the compound of the present invention obtained in Example 6.

IR: the chart is shown in FIG. 6.
The characteristic absorptions were as follows:
νc=o: 1,725 cm$^{-1}$
νc=c: 1,635 cm$^{-1}$
νC—F: 1,100 to 1,300 cm$^{-1}$ From the above results, it was confirmed that the obtained compound is represented by the following formula:

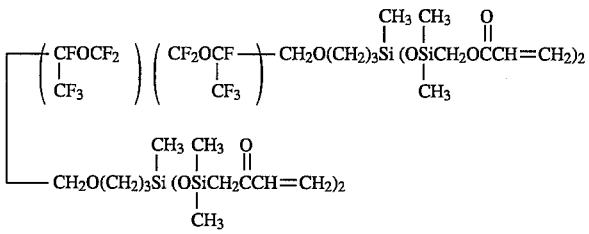

Example 7

The procedure was the same as in Example 1, except that in place of the fluorine-containing organosilicon compound represented by the above formula (2-1), 29.2 g of a fluorine-containing organosilicon compound represented by the following formula (2-7):

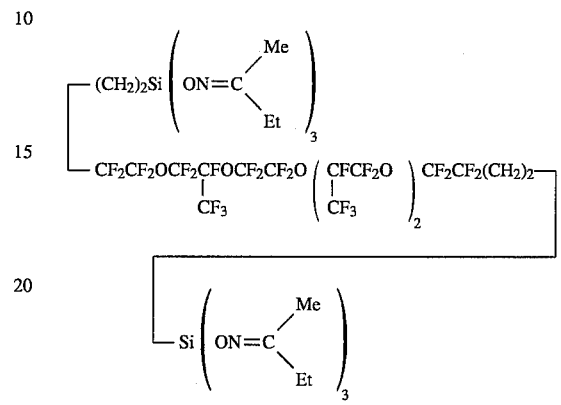

(2-7)

and in place of the guanidine derivative (condensation catalyst) represented by the above formula (6), 0.06 g of a dibutyl tin dilaurate (condensation catalyst) were charged into a 100-ml three-necked flask, and 13.3 g of a 50% solution of the organosilicon compound of the formula (3-1) used in Example 1 in toluene was placed in a dropping funnel, thereby obtaining 41.3 g of a pale yellow transparent liquid. This was analyzed by $^1$H-NMR, $^{19}$F-NMR, and IR and the following results were obtained:

$^1$H—NMR: TMS standard

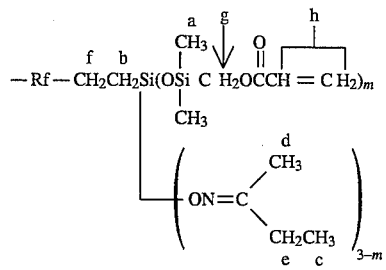

a: 0.17 ppm (s, 23.28H)
b: 0.91 ppm (m, 4H)
c: 1.07 ppm (t, 6.36H)
d: 1.84 ppm (s, 6.36H)
e: 2.28 ppm (q, 4.24H)
f: 2.35 ppm (m, 4H)
g: 3.77 ppm (s, 7.76H)
h: 5.5 to 6.5 ppm (m, 11.64H)

$^{19}$F—NMR: CF$_3$COOH standard

Figure 7:
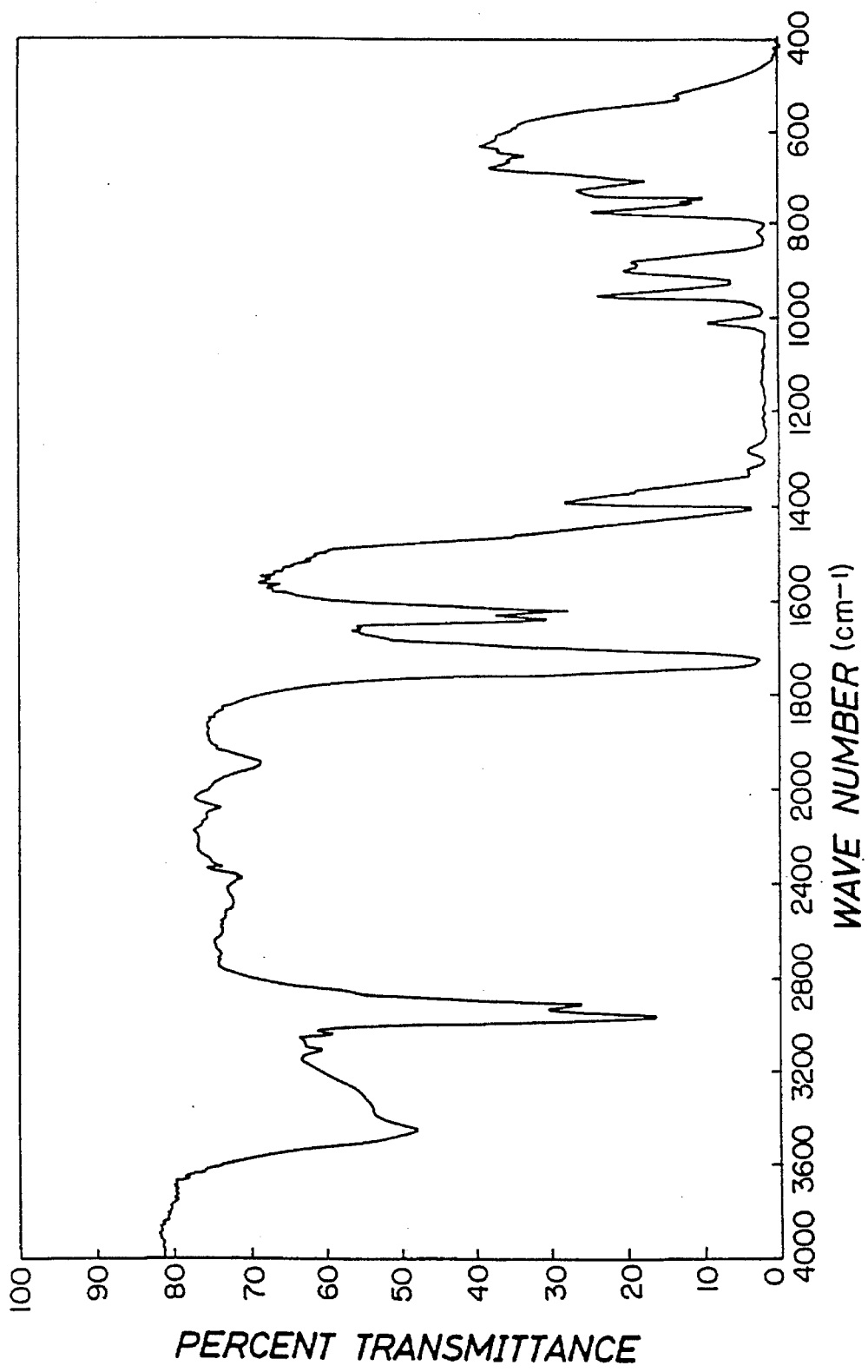
FIG. 7 ms an IR chart of the compound of the present invention obtained in Example 7.

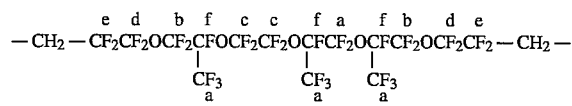

a: −3.59 ppm
b: −6.62 ppm
c: −9.37 ppm
d: −10.78 ppm
e: −43.11 ppm
f: −68.07 ppm IR: the chart is shown in FIG. 7.
The characteristic absorptions were as follows:

$\nu_{C=O}$: 1,725 cm$^{-1}$ $\nu_{C=C}$: 1,635 cm$^{-1}$ $\nu_{C-F}$: 1,100 to 1,300 cm$^{-1}$

From the above results, it was confirmed that the obtained compound is represented by the following formula:

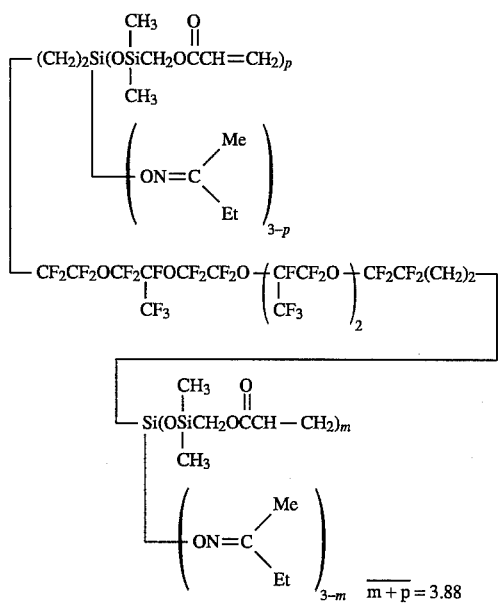

Example 8

The procedure was the same as in Example 1, except that in place of the fluorine-containing organosilicon compound represented by the above formula (2-1), 41.4 g of a fluorine-containing organosilicon compound represented by the following formula (2-8):

$$(MeO)_3Si(CH_2)_3NHC(O)\left[\left(CFOCF_2\atop CF_3\right)_i\left(CF_2OCF\atop CF_3\right)_j\right]C(O)NH(CH_2)_3Si(OMe)_3 \quad i+j=10 \quad (2\text{-}8)$$

and 0.05 g of the guanidine derivative (condensation catalyst) represented by the above formula (6) were charged into a 100-ml three-necked flask, and 26.6 g of a 50 % solution of the organosilicon compound of the formula (3-1) used in Example 1 in toluene was placed in a dropping funnel, thereby obtaining 63.5 g of a pale yellow transparent liquid. This was analyzed by $^1$H-NMR, $^{19}$F-NMR, and IR and the following results were obtained:

$^1$H—NMR: TMS standard

-continued $$-Rf-\overset{O}{\overset{\|}{C}}\overset{h}{N}H\overset{d}{C}H_2\overset{c}{C}H_2\overset{b}{C}H_2Si(O\overset{a}{\underset{|}{S}i}\overset{CH_3}{\underset{|}{C}}\overset{f}{H_2O}\overset{O}{\overset{\|}{C}}CH\overset{g}{=CH_2})_m$$
$$\underset{e}{\underset{|}{(OCH_3)_{3-m}}}$$

a: 0.17 ppm (s, 23.70H)
b: 0.52 ppm (m, 2H)
c: 1.63 ppm (m, 2H)
d: 3.34 ppm (m, 2H)
e: 3.46 ppm (s, 6.15H)
f: 3.75 ppm (s, 7.90H)
g: 5.5 to 6.5 ppm (m, 11.85H)
h: 7.52 ppm (bs, 1H)
$^{19}F$—NMR: $CF_3COOH$ standard $$-\underset{b}{\overset{d}{CF}}\underset{CF_3}{\overset{|}{\underset{|}{-}}}(O\overset{a}{CF_2}\underset{CF_3}{\overset{e}{\underset{|}{CF}}})_{i-1}OCF_2CF_2O\underset{a}{-}(\overset{e}{CF}\underset{CF_3}{\overset{a}{\underset{|}{CF_2O}}})_{j-1}\underset{CF_3}{\overset{d}{\underset{|}{CF}}}-$$

$i + j = 10$ a: −3.50 ppm
b: −5.97 ppm
c: −9.37 ppm
d: −55.63 ppm
e: −67.81 ppm

Figure 8:
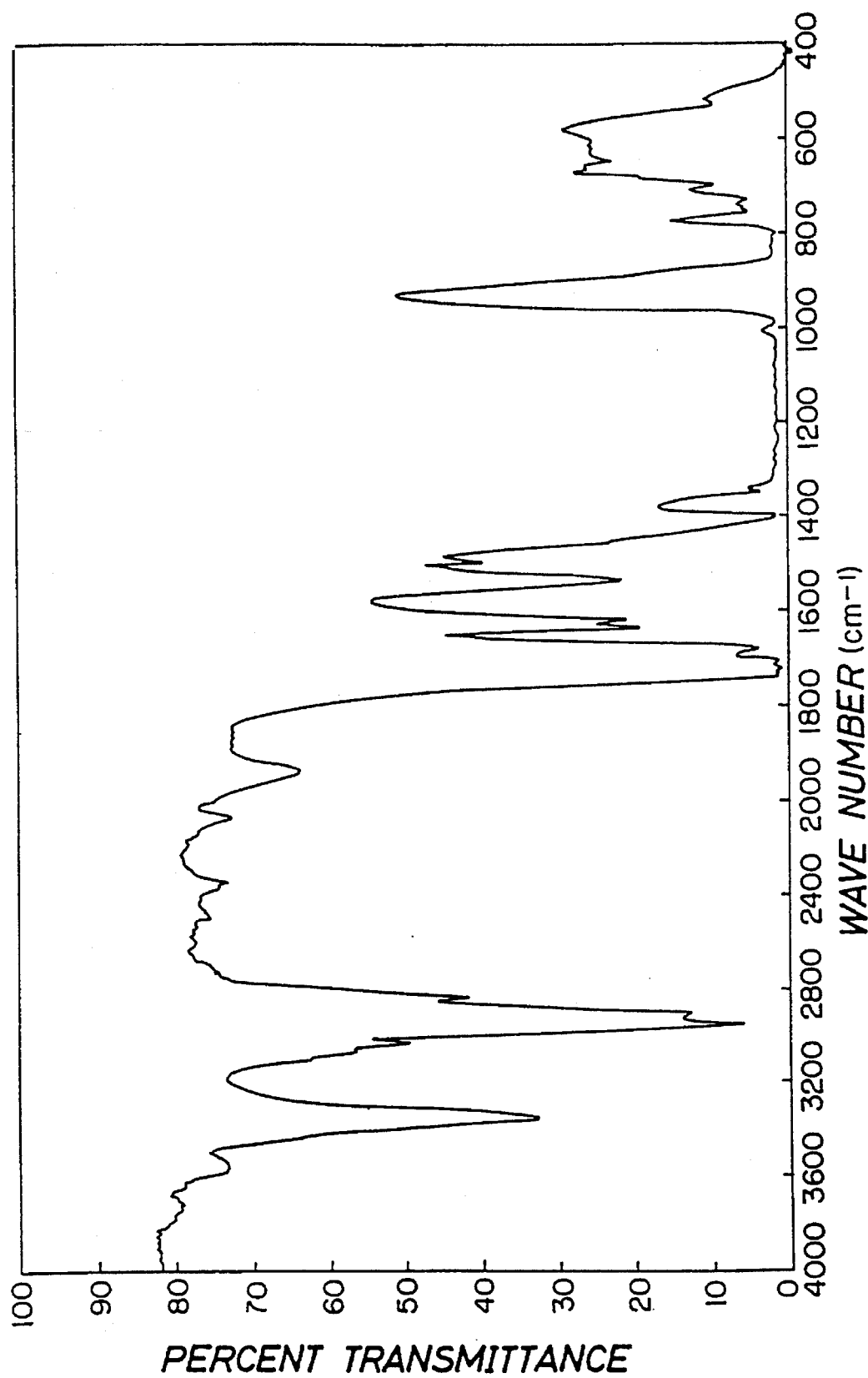
FIG. 8 is an IR chart of the compound of the present invention obtained in Example 8.

IR: the chart is shown in FIG. 8.
The characteristic absorptions were as follows:
vN—H: 3,350 $cm^{-1}$
vC=O (acryloyl): 1,725 $cm^{-1}$
vC=O (amide): 1,710 $cm^{-1}$
vC=C: 1,635 $cm^{-1}$
vN—H: 1,535 $cm^{-1}$
vC—F: 1,100 to 1,300 $cm^{-1}$ From the above results, it was confirmed that the obtained compound is represented by the following formula:

$$\left[\underset{CF_3}{\overset{|}{\underset{|}{(CFOCF_2)}}}_i\underset{CF_3}{\overset{|}{\underset{|}{(CF_2OCF)}}}_j\overset{O}{\overset{\|}{C}}NH(CH_2)_3Si(O\overset{CH_3}{\underset{|}{Si}}CH_2O\overset{O}{\overset{\|}{C}}CH=CH_2)_m\right]$$
$$\underset{|}{(OCH_3)_{3-m}}$$
$$-\overset{O}{\overset{\|}{C}}NH(CH_2)_3Si(O\overset{CH_3}{\underset{|}{Si}}CH_2O\overset{O}{\overset{\|}{C}}CH=CH_2)_p$$
$$\underset{|}{(OCH_3)_{3-p}}$$

$i + j = 10$
$m + p = 3.95$

What is claimed is:

1. A fluorine-containing organosilicon compound represented by the following general formula (1):

$$Rf\left[-A-\underset{X_{3-m-n}}{\overset{R^1_m}{\underset{|}{Si}}}(O\overset{CH_3}{\underset{|}{Si}}CH_2O\overset{O}{\overset{\|}{C}}CH=CH_2)_n\right]_Y \quad (1)$$

wherein Rf represents a perfluoroalkyl group, a perfluorooxyalkyl group, a perfluoroalkylene group, or a perfluorooxyalkylene group, A represents a bivalent organic group, $R^1$ represents an unsubstituted or substituted monovalent hydrocarbon group, X represents a hydrolyzable group, Y is 1 in the case where the above group Rf represents a perfluoroalkyl group or a perfluorooxyalkyl group or Y is 2 in the case where the above group Rf represents a perfluoroalkylene group or a perfluorooxyalkylene group, m is an integer of 0 to 2, and n is an integer of 1 to 3, with m+n being 3 or less.

2. The fluorine-containing organosilicon compound of claim 1, wherein said fluorine-containing organosilicon compound represented by the following general formula (4):

$$Rf-A-\underset{X_{3-m-n}}{\overset{R^1_m}{\underset{|}{Si}}}(O\overset{CH_3}{\underset{|}{Si}}CH_2O\overset{O}{\overset{\|}{C}}CH=CH_2)_n \quad (4)$$

wherein Rf represents a perfluoroalkyl group or a perfluorooxyalkyl group and A, $R^1$, X, m, and n have the same meanings as defined above.

3. The fluorine-containing organosilicon compound of claim 1, wherein said fluorine-containing organosilicon compound represented by the following general formula (5):

$$(CH_2=CH\overset{O}{\overset{\|}{C}}OCH_2\underset{CH_3}{\overset{CH_3}{\underset{|}{Si}}}O)_n\underset{X_{3-m-n}}{\overset{R^1_m}{\underset{|}{Si}}}-A-Rf''-A-\underset{X_{3-p-q}}{\overset{R^1_p}{\underset{|}{Si}}}(O\underset{CH_3}{\overset{CH_3}{\underset{|}{Si}}}CH_2O\overset{O}{\overset{\|}{C}}CH=CH_2)_q \quad (5)$$

wherein Rf" represents a perfluoroalkylene group or a perfluorooxyalkylene group, p is an integer of 0 to 2, q is an integer of 1 to 3, with p+q being 3 or less, A each independently represent a bivalent organic group, $R^1$ each independently represent an unsubstituted or substituted monovalent hydrocarbon group, X each independently represent a hydrolyzable group, and m and n have the same meanings as defined above.

4. The fluorine-containing organosilicon compound of claim 2, wherein in the general formula (4) said Rf represents a perfluoroalkyl group or perfluorooxyalkyl group having 1 to 30 carbon atoms.

5. The fluorine-containing organosilicon compound of claim 2, wherein in the general formula (4) said Rf represents a perfluoroalkyl group having 1 to 12 carbon atoms.

6. The fluorine-containing organosilicon compound of claim 2, wherein in the general formula (4) said Rf represents a perfluorooxyalkyl group having 2 to 20 carbon atoms.

7. The fluorine-containing organosilicon compound of claim 3, wherein in the general formula (5) said Rf" represents a perfluoroalkylene group or perfluorooxyalkylene group having 1 to 100 carbon atoms.

8. The fluorine-containing organosilicon compound of claim 3, wherein in the general formula (5) said Rf" represents a perfluoroalkylene group having 2 to 12 carbon atoms.

9. The fluorine-containing organosilicon compound of claim 3, wherein in the general formula (5) said Rf" represents a perfluorooxyalkylene group having 10 to 100 carbon atoms.

10. The fluorine-containing organosilicon compound of claim 2, wherein in the general formula (4) said A represents a bivalent hydrocarbon group having 2 to 10 carbon atoms.

11. The fluorine-containing organosilicon compound of claim 2, wherein in the general formula (4) said A represents —$CO_2$—$(CH_2)_3$—, —$CH_2O$—$(CH_2)_3$—, —CONH—$(CH_2)_3$—, or

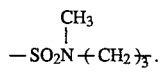

12. The fluorine-containing organosilicon compound of claim 3, wherein in the general formula (5) said A represents a bivalent hydrocarbon group having 2 to 10 carbon atoms.

13. The fluorine-containing organosilicon compound of claim 3, wherein in the general formula (5) said A represents —$CO_2$—$(CH_2)_3$—, —$CH_2O$—$(CH_2)_3$—, —CONH—$(CH_2)_3$—, or

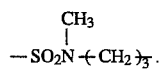

14. The fluorine-containing organosilicon compound of claim 2, wherein in the general formula (4) said $R^1$ represents an unsubstituted or substituted monovalent hydrocarbon group having 1 to 6 carbon atoms.

15. The fluorine-containing organosilicon compound of claim 3, wherein in the general formula (5) said $R^1$ represents an unsubstituted or substituted monovalent hydrocarbon group having 1 to 6 carbon atoms.

16. The fluorine-containing organosilicon compound of claim 2, wherein in the general formula (4) said X represents a chlorine atom, a methoxy group, an ethoxy group, an acetoxy group, a propenoxy group, an isopropenoxy group, a diethylamino group, or

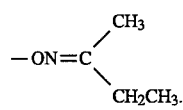

17. The fluorine-containing organosilicon compound of claim 3, wherein in the general formula (5) said X represents a chlorine atom, a methoxy group, an ethoxy group, an acetoxy group, a propenoxy group, an isopropenoxy group, a diethylamino group, or

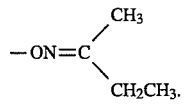

18. A method of producing the fluorine-containing organosilicon compound represented by the above general formula (1), comprising reacting a hydrolyzable silane compound represented by the following general formula (2):

wherein Rf, A, m, $R^1$, X, and Y have the same meanings as defined above in the above general formula (1) with a silane compound represented by the following general formula (3):

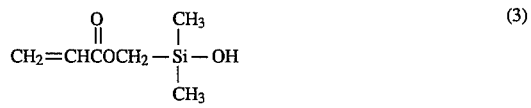

in the presence of a condensation catalyst.

19. The method of producing the fluorine-containing organosilicon compound of claim 18, wherein the hydrolyzable silane compound of said general formula (2) is a hydrolyzable silane compound represented by the following formula:

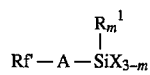

wherein Rf', A, X, $R^1$, and m have the same meanings as defined above.

20. The method of producing the fluorine-containing organosilicon compound of claim 18, wherein the hydrolyzable silane compound of said general formula (2) is a hydrolyzable silane compound represented by the following formula:

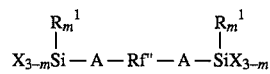

wherein Rf", A, X $R^1$, and m have the same meanings as defined above.

* * * * *